United States Patent [19]
Oxley

[11] Patent Number: 5,364,598
[45] Date of Patent: * Nov. 15, 1994

[54] SYSTEM FOR SAMPLING FLUID

[75] Inventor: L. Thomas Oxley, Riverwoods, Ill.

[73] Assignee: T-Systems, Inc., Riverwoods, Ill.

[*] Notice: The portion of the term of this patent subsequent to Feb. 8, 2011 has been disclaimed.

[21] Appl. No.: 738,071

[22] Filed: Jul. 30, 1991

[51] Int. Cl.⁵ .............................................. G01N 35/02
[52] U.S. Cl. ................................ 422/102; 422/63; 422/65; 422/100; 422/103; 436/43; 436/47; 436/48; 436/807; 436/180
[58] Field of Search ............... 422/102, 100, 103, 104, 422/99, 63, 81–83, 83.5, 88, 89, 64, 65; 436/174, 180, 43, 47, 48, 807; 141/329, 330

[56] References Cited

U.S. PATENT DOCUMENTS

| | | | |
|---|---|---|---|
| 3,105,613 | 10/1963 | Barton et al. | 222/81 |
| 3,239,104 | 3/1966 | Scholle | 222/81 |
| 4,109,829 | 8/1978 | Kuckens et al. | 222/81 |
| 4,240,482 | 12/1980 | Andersson et al. | 222/561 X |
| 4,458,733 | 7/1984 | Lyons | 141/1 |
| 4,607,671 | 8/1986 | Aalto et al. | 141/329 |
| 4,738,826 | 4/1989 | Harris | 422/100 |
| 4,750,643 | 6/1988 | Wortrich | 222/81 |
| 4,776,488 | 10/1988 | Gurzan | 222/81 |
| 4,808,381 | 2/1989 | McGregor et al. | 422/100 |
| 4,911,329 | 3/1990 | Canini | 222/81 |
| 5,012,845 | 5/1991 | Averette | 141/329 |
| 5,151,184 | 9/1992 | Ferkany | 210/514 |

Primary Examiner—James C. Housel
Assistant Examiner—Long V. Le
Attorney, Agent, or Firm—Reinhart, Boerner, Van Deuren, Norris & Rieselbach

[57] ABSTRACT

An automated system for sampling and testing a fluid specimen using an analysis station. The fluid specimen is collected in a flexible container having an access port. A piercing element pierces the access port and is withdrawn, allowing the fluid specimen to drain from the container. Subsequently, the container can be resealed.

7 Claims, 7 Drawing Sheets

SYSTEM FOR SAMPLING FLUID

The present invention is concerned generally with a system for accumulating, dispensing and analyzing a fluid specimen. More particularly, the invention is concerned with a system having a container for automated sampling and/or dispensing of fluid specimens for chemical analysis and specimen testing probes allowing self contained analysis for the presence of undesirable substances.

Analysis for substances in a specimen involves collection and/or dispensing, and also analysis of a specimen, typically a fluid. Labels can be attached to the exterior of the container and/or to a coupled remote or holding container in selected instances. A lab technician can include on the label the source of the specimen, the date of collection and other relevant data for use in analysis of the specimen. Analysis of any specimen using a container usually requires additional preparatory steps, including, for example, (a) creation of a new record of information for each analytical procedure performed on the specimen, and in some instances also maintaining the legal chain of evidence for the specimen, (b) physical apportionment of the initially collected specimen into a plurality of specimens for a number of different analytical evaluations, and (c) maintenance of the chemical integrity of the specimen during and after subdivision into a plurality of specimens undergoing different tests in an analytical process. There is a strong and growing demand for large scale testing programs, such as in chemical plants and food product manufacturing facilities. Such a substantial increase in the demand for testing programs will place a great premium on improved economics, efficiency and reliability, and in some cases will require strict integrity of the legal chain of specimen custody.

It is therefore an object of the invention to provide an improved method and system for accumulating a specimen for ascertaining the presence of selected chemical substances and/or biological materials.

It is another object of the invention to provide a novel specimen system for transferring specimens to and/or from a single or multicompartment plastic container for analysis.

It is an additional object of the invention to provide various sampling and test devices attachable to or detachable from a container enabling the easy sampling and analysis of a specimen, including separate use thereof or in conjunction with a separate plastic container for analysis.

It is yet another object of the invention to provide an improved system using a plastic container having dispenser elements and access ports which allow destructive access through the container to the specimen.

It is an additional object of the invention to provide a novel fluid specimen processing system for accumulating fluid specimens and selectively accessing the specimen in the container with a piercing device enabling automated dispensing to an analytical receptacle for automated analysis.

Other objects, features and advantages of the present invention will be readily apparent from the following description of the preferred embodiments thereof, taken in conjunction with the accompanying drawings described below wherein like elements have like numerals throughout the several views.

DETAILED DESCRIPTION OF PREFERRED EMBODIMENTS

Figure 5A:
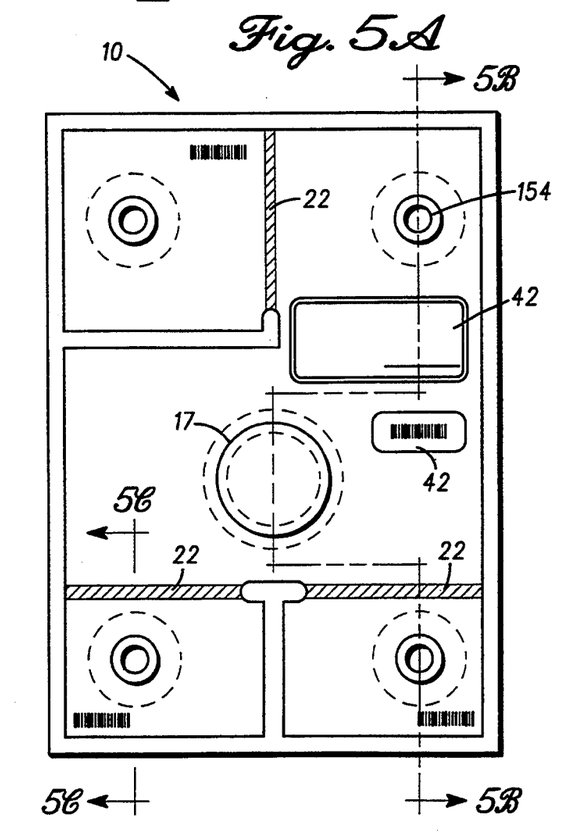
FIG. 5A shows a plastic container in a plan view with various access ports.
Figure 5B:
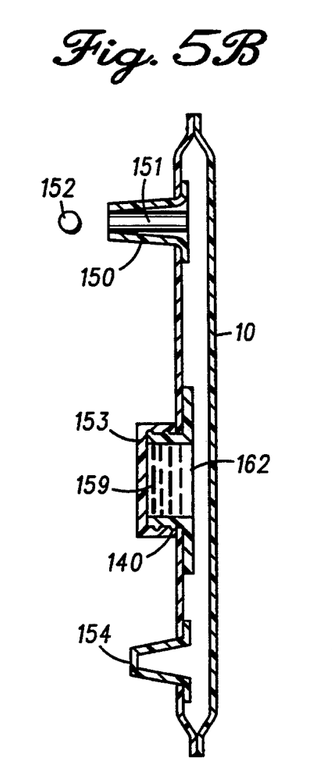
FIG. 5B illustrates a side view of the plastic container showing the details of the access ports.
Figure 5C:
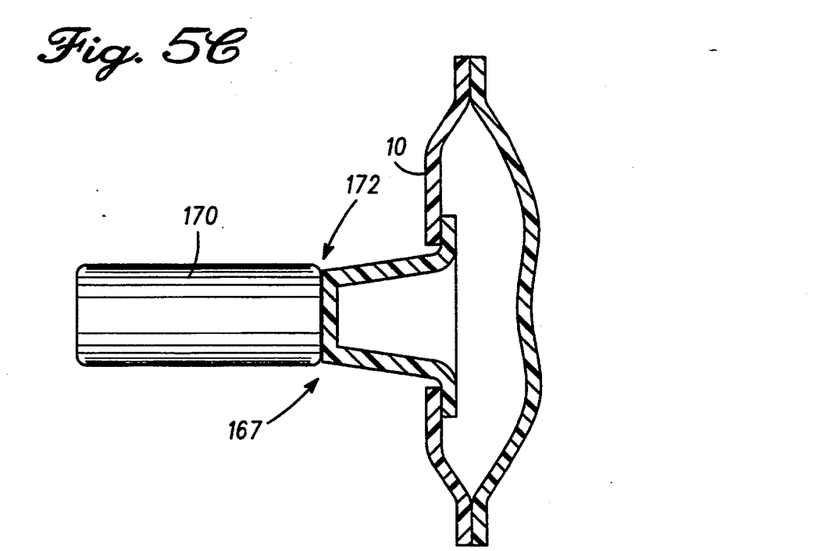
FIG. 5C shows a partial side view of another one of the access ports shown along section cross section taken along 5C—5C in FIG. 5A.
Figure 6A:
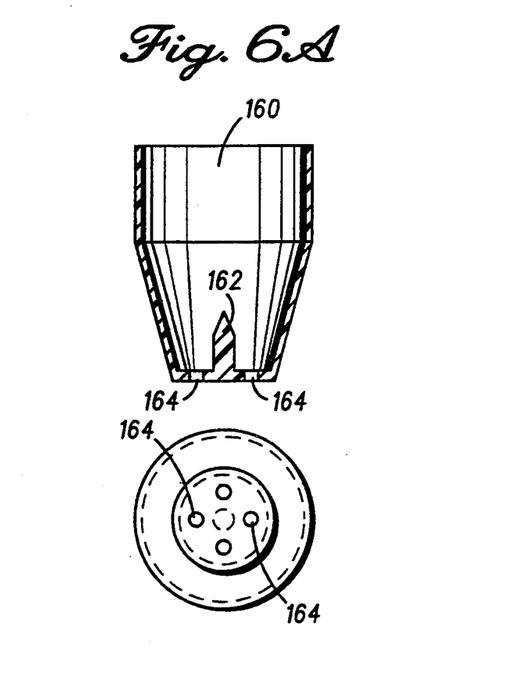
FIG. 6A illustrates a puncture and draining element in side cross section and top view and FIG. 6B shows a sequence of operational steps in a method of using one of the access ports in FIG. 5A to access a specimen by means of the puncture element of FIG. 6A.
Figure 6B:
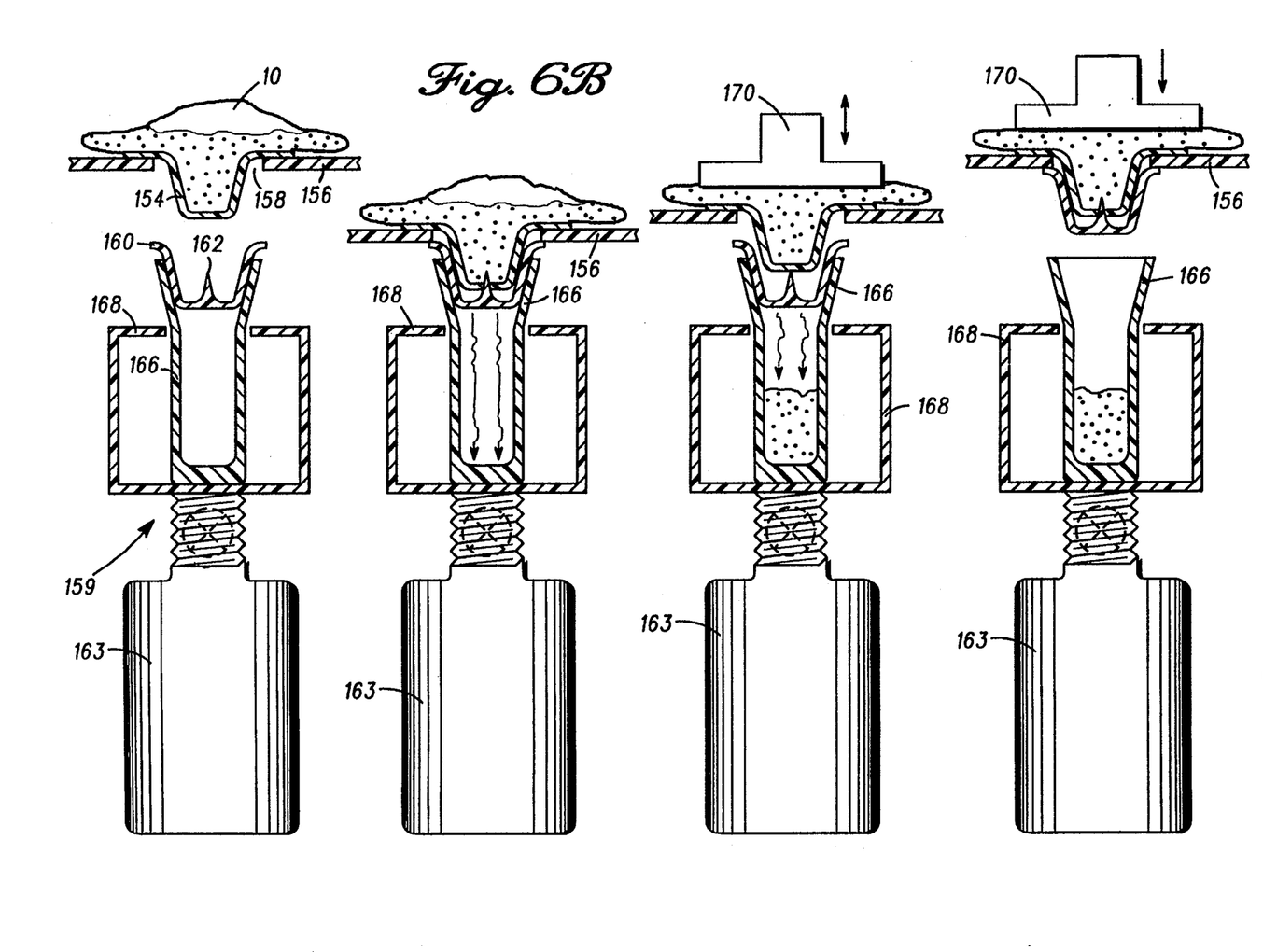
Figures 7, 8A, 8B, 8C, 8D, 8E:
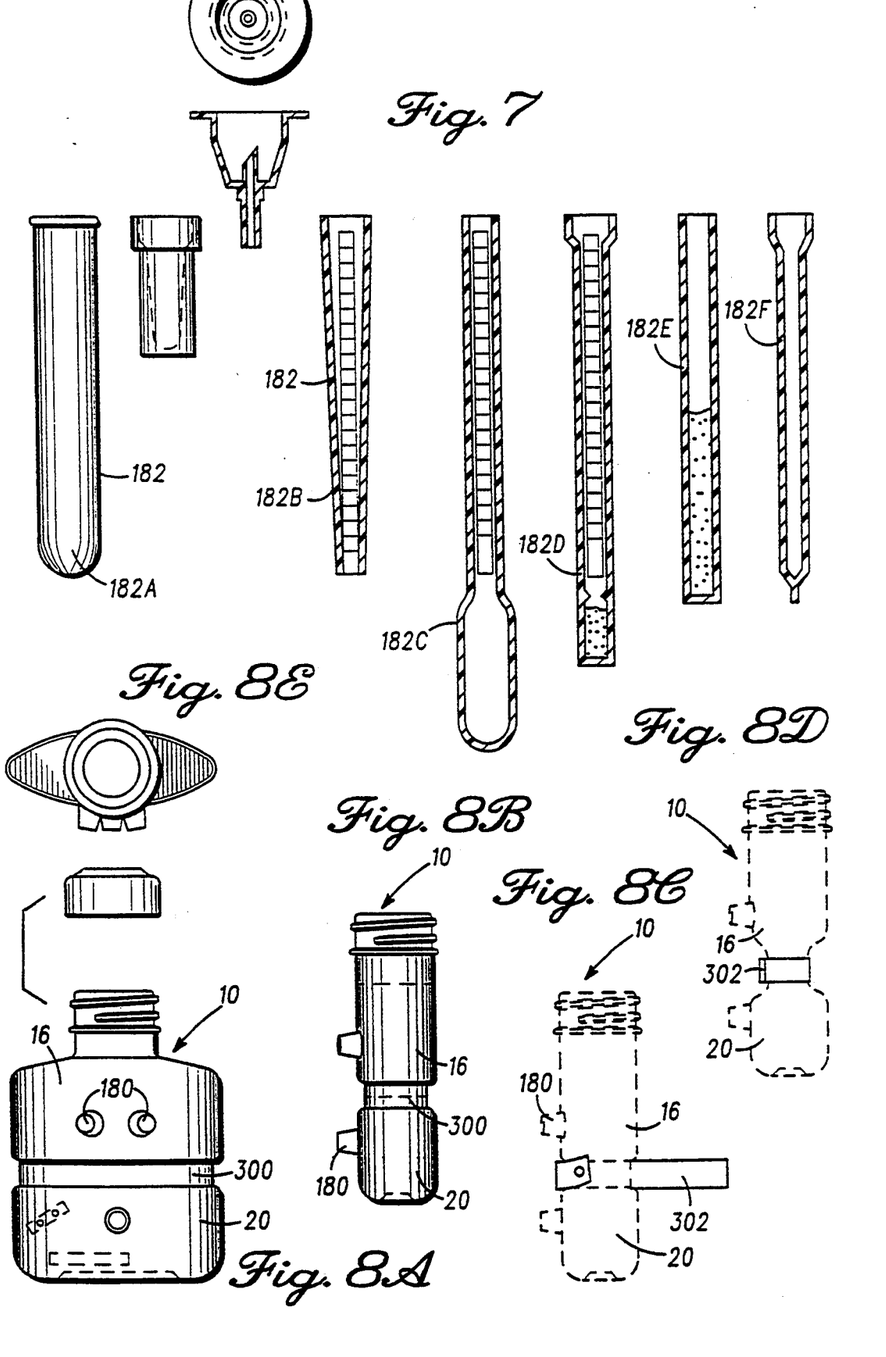
FIG. 7 illustrates a plurality of probe test devices which can be used as attachments to a separate specimen source or can be used independently for fluid specimen testing.
FIG. 8A shows a front view of an injection molded container having access ports and an indentation band.
FIG. 8B is a side view of the container of FIG. 8A.
FIG. 8C shows another side view of a container such as is shown in FIG. 8A with an indentation band being applied.
FIG. 8D shows the container of FIG. 8C with the identation band more tightly attached than in FIG. 8B.
FIG. 8E is a top and side view of the cap portion of the containers of FIG. 8.

Referring to the drawings and in particular to FIGS. 5, 6 and 8, a multicompartment plastic container, such as a plastic container 10, constructed in accordance with the invention is generally indicated. Collection and analysis of specimens having undesirable (or conversely, specifically desired) chemicals or biological substances (hereinafter all of the above are an "undesirable substance") is accomplished by utilizing one of the illustrated multicompartment plastic containers 10 (hereinafter "the plastic container 10"). In order to carry out determination of the presence of an undesirable substance, the plastic container 10 functions first to collect a specimen taken from the subject source, such as a storage container, a chemical processing line, a food products container or even water from a polluted body of water. Various conventional means can be used to initially collect the specimen.

The plastic container 10 includes an upper container section 16 having an opening at one end (shown generally as 18 in FIG. 1) to enable receiving the fluid specimen potentially containing the substance of interest. Accumulation of the specimen is accomplished by conventional means, such as, funnels or transfer lines (not shown). Alternatively, as shown in FIG. 5A an open flange 17 is sealingly engaged to the plastic container 10 and supports the top of the plastic container 10. The specimen can be input via the opening of the flange 17. Once the specimen has been collected, a seal cap 153 (see FIG. 5B) can be sealingly coupled to the flange 17.

Once the fluid specimen has been accumulated, it can be moved within the upper container section 16 to apportion the specimen. This apportionment can take place in both the upper container section 16 and selected portions of the lower container section 20 (see FIG. 1). In the preferred embodiment the plastic container 10 can be sealed at the top to preserve the specimen integrity before apportioning the specimen in the various container sections or subcompartments. In an alternative embodiment one can choose to apportion the fluid specimen between the container sections before sealing at the top.

The ability to apportion the collected fluid specimen among the various container sections enables establishing a plurality of different specimens for scientific reliability and legal requirements. The apportionment also can be useful if some prescreening tests are to be done on the fluid specimen to eliminate the need to perform complete testing on a large number of specimens.

Figure 1:
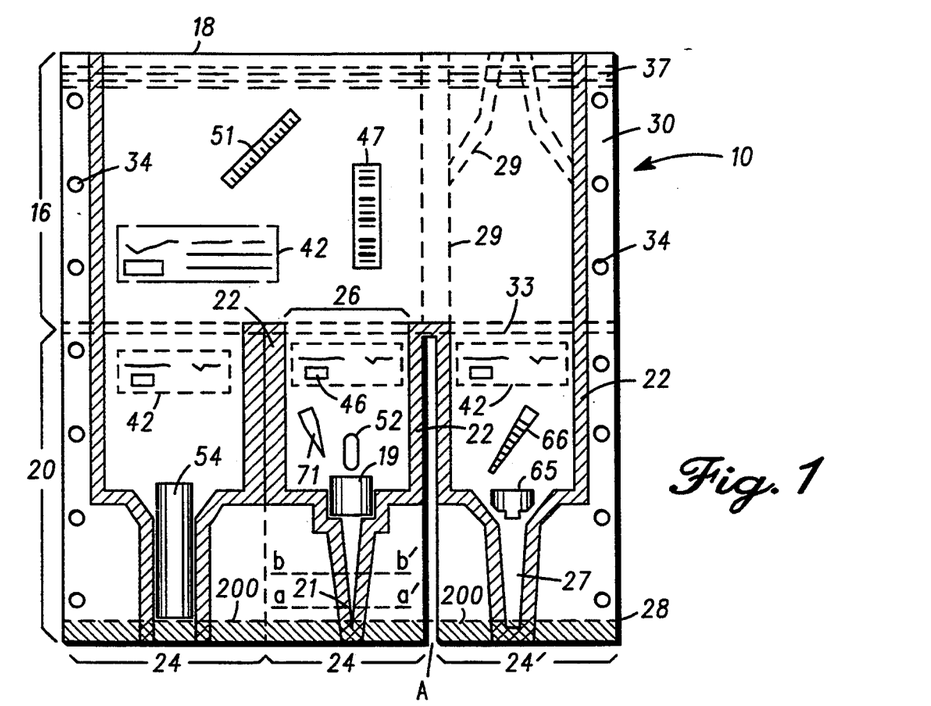
FIG. 1 is a front elevation of a multicompartment plastic bag container constructed in accordance with one form of the invention.
Figure 2:
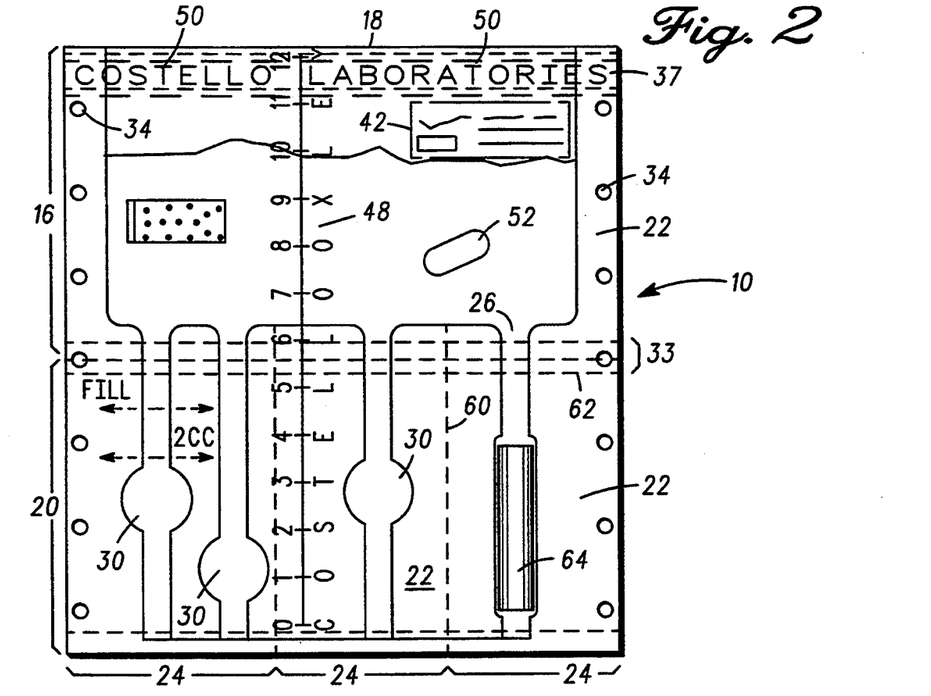
FIG. 2 illustrates a front elevation of a multicompartment plastic container having a plurality of pouch or pocket elements.

To accomplish the apportionment of the fluid specimen within the various container sections, the lower container section 20 is initially at least partially open to the upper container section 16 via, for example, opening 26 as shown in FIG. 2. These openings are defined by noting the location of cross-hatched seal areas 22 in the lower container section 20 as shown in FIG. 1. In the preferred embodiment these seal areas 22 are nonreusable heat seals formed by the manufacturer prior to shipment to the customer and accomplished by use of any one of a variety of conventional available devices, such as heat sealing the plastic or through injection molding methods of manufacture. Access to the fluid specimen must therefore proceed by a destruction of some part of the plastic container 10.

As seen in FIG. 2, the container design can accommodate various subcompartments 24 in the lower container section 20 and provide the opening 26 between the upper and lower container sections, 16 and 20, respectively. One can also use the seal areas 22 to provide different design configurations of subcompartments and even provide additional shapes adjunct to the subcompartments, such as a spout 27 for the subcompartments 24 (see FIG. 1). The spout 27 is usable by merely cutting along one line chosen anywhere above a lower seal line 28 and across the mouth of the spout 27.

In another form of construction of the plastic container 10, the spout 27 can be accessed by merely tearing along a line of perforations 200, such as along line 28 as shown in FIG. 1. In this manner, one can manually remove part of the plastic container 10, and thus one does not have to use scissors or any cutting implement which might be contaminated from previously opening a container containing a specimen having a contaminant therein.

In addition to the illustrated layout for the container seal areas 22 provided by the manufacturer, the customer, or even the analytical laboratory user, can select alternative seal designs which can be implemented by various known means. A customer can thus select and prepare a custom design by using a predetermined container size and a conventional manually operating heat sealing device (not shown) having a seal bar design in the intended geometry of the final seal areas 22. The plastic container 10 can therefore include a plurality of different optional heat seal line patterns 29 (see FIG. 1) disposed on the plastic container 10. One can, for example, use different seal line markings (dashed, dotted, and color encoded) to denote different available seal patterns. The various heat seal line patterns 29 can then be implemented by, for example, (a) using manually guided heat seal means, (b) using the heat sealing device 36 having an appropriate seal design pattern (described above), (c) employing a conventional machine control system to perform heat seal line tracing which seals along one of the given marked seal line patterns 29 or (d) using other sealing means creating nonreusable seals.

The ability to construct a variety of functional shapes as part of, and in combination with, the plastic container 10 can further include, for example, a pipette design 21 in FIG. 1. In FIG. 1 once the opening 26 of the plastic container 10 has been sealed to form a subcompartment 24 filled with the fluid specimen, the pipette design 21 in FIG. 1 allows dispensing small portions of the fluid specimen. This can be done by first cutting along the lower seal line 28 (or along lines aa' or bb' for larger openings). In an alternate embodiment discussed hereinbefore, the user can manually separate the plastic container 10 above the lower seal line 28 by virtue of the perforations 200.

Tubing 19 (center bottom of FIG. 1) provides support for the surrounding plastic container 10 and enables controllably displacing substances in the center subcompartment 24 and dispensing small portions of the specimen for testing. Such a pipette type of combined shape can be used with other conceivable designs to enhance container operation and analysis of the specimen. Further useful shapes can also include, for example, a pocket or pouch element 30 in the lower container section 20 (see FIG. 2). This pouch element 30 is defined by at least one plastic layer portion 31 being discontinuous relative to the plane of the plastic layer of the plastic container 10. The pouch element 30 is fillable with the specimen to provide a locally enlarged substance volume and increased substance optical path length. This structural feature therefore allows accumulation of sufficient substance quantities to perform analytical procedures not normally accomplishable with relatively thin layers of unknown layer thicknesses of the specimen present within the plastic container 10.

Additional functional shapes therefore allow well controlled analysis of known specific volumes and known particular optical path lengths of the specimen. For example, the Color Eye 3000 spectrophotometer (manufactured by Macbeth Ltd., Newburgh, N.Y.) can be used to perform analysis through transparent & translucent plastic layers of containers holding such a specimen.

The analytical technician can also easily remove, by means such as a syringe or pipette, a substantial and known volume of the specimen. To this end the plastic container 10 also lends itself to inclusion of various precise volume indicators imprinted in association with the pouch element 30 (see, for example, FIG. 2A left most subcompartment 24 with the 2cc indicator marking).

The subcompartments 24 defined by the design of the plastic container 10 can be selectively filled in the manner described hereinbefore: the technician can move the specimen between the upper container section 16 and lower container section 20 and then through the openings 26 into each of the desired subcompartments 24. Either before or after the technician has apportioned the specimen in the desired sections of the plastic container 10, means for making a seal can be used to seal the lower container section 20. This is accomplished by sealing along center seal area 33 as shown in FIG. 2. In addition, as described hereinbefore, the plastic container 10 can be completely closed by sealing the upper seal area 37.

In another form of the invention shown in FIG. 8, the container 10 is formed (such as by injection molding) with an indentation band 300 which allows easy sealing along the band 300 to form separate compartments containing a specimen. The indentation band 300 also permits use of a tightening band 302 which allows compression of the injection molded plastic. After collection and sealing of a fluid specimen in the container 10, the bond 302 can be released causing formation of a slight vacuum. This condition helps minimize the possibility of forming a gas overpressure condition and also makes it easier to effectuate a good seal, not having to construct the container 10 or generate increased pressure due to loss of container volume upon sealing into plural compartments.

The technician can commence the chemical or biological analysis process by separating selected ones of the subcompartments 24 and/or the upper container section 16. Separation occurs by destructive means and can be accomplished by, for example, cutting with scissors or separating along a prepared tear line. In an alternate embodiment as discussed hereinbefore, the user can manually separate the plastic container 10 along the lower seal line 28 by virtue of the perforations 200. In another form of the invention the subcompartments 24 can be removed by merely cutting along one line since they are already separated by the manufacturer along another line (see, for example, open area denoted A for subcompartment 24' in FIG. 1). The plastic container 10 is preferably an optically transparent or visually translucent material allowing use of any one of a variety of conventional optical analysis procedures on the specimen (for example, the Color Eye 3000 described hereinbefore). Such optical analysis procedures can also include, for example, simple naked eye observations as well as optical absorption spectrophotometry.

The plastic container 10 and the fittings in contact with the specimen also should be inert to the substance contained therein to avoid chemical modification or contamination. The plastic container 10 should further allow long-term cold storage and freezing, while maintaining the physical and chemical integrity of the specimen. Numerous conventional thermoplastic materials fulfill these requirements and an example of such a material is "Saran" coated polyester with an exterior coating of polyethylene.

As mentioned generally before, the ability to collect the specimen in the upper container section 16 (see FIG. 1) and in various ones of the subcompartments 24 enables performance of a plurality of different tests and maintenance of a reference standard or reference substance and backup standards. The upper container section 16, for example, can be used for holding a substance for preliminary screening or overflow. The specimens in the subcompartments 24 can, for example, be used for preliminary, primary and confirmatory analyses and also for long-term backup analysis. The ability to use numerous subdivided specimens allows a thorough analysis of the specimen. The ability to have a backup specimen provides a sound evidentiary position when needed to legally and scientifically establish thee presence of chemicals, diseases, or other undesirable chemicals in a specimen.

Scientific objectives for substance analysis are met by virtue of the redundancy of available specimens, the performance of multiple specimen analyses and maintenance of a reference or backup specimen. Legal objectives are met by providing clear evidence of the identity of a specimen and unbroken chain of custody over the cycle of collection of the specimen and the performance of numerous analytical procedures. This custodial objective is accomplished in part by inclusion of all identification element on any one or more parts of a surface of the plastic container 10. The identification element can be, for example, a writeable area 42 for entering information identifying the source of the specimen, a signature box for the donor and locations for entry of the identity and signature of each party in the chain of specimen custody. This writeable area 42 also is preferably on each of the separate sections of the plastic container 10 in order to establish identity and custody of each specimen portion. Additional identification can be provided by other means, such as, by bar code serial numbers 46 or labels 47 attached to, or imprinted on, each of the separable container subcompartments 24 and/or on the upper container section 16 (see FIG. 1).

In order to prevent tampering with the specimen once it has been collected, the plastic container 10 includes a first tampering indicator means which can be an embossed or imprinted code 50 along the top seal area 37 of the plastic container 10 (see FIG. 2).

In another aspect of the invention, certain tests can be performed on the specimen substance in order to diminish the number of "suspect" specimens which must undergo more detailed and costly analysis. Such a test can be performed on the specimen collected in any of the subcompartments 24 or the upper section 16 of the plastic container 10. As described hereinbefore in one of the preferred embodiments shown in FIGS. 1 and 2, the specimens are apportioned in the subcompartments 24 after the upper container section 16 is sealed from the outside environment. Once the specimen is apportioned, the subcompartments 24 are sealed and isolated from each other and also from the upper container section 16. Isolation of the various specimens also can enable testing to proceed on each specimen wholly within the container which also diminishes the possibility of contamination of the specimen or of chemical contamination or disease transmission to a technician performing the analysis.

Prescreening procedures can involve simple tests, such as, checking the temperature of a liquid specimen by use of a conventional thermal strip indicator 51 (see FIG. 1) or checking pH of the specimen by the use of pH sensitive indicator strips (see FIG. 7). Rather than including pH strips, temperature sensors or other such indicators as separate components loosely disposed within the plastic container 10, such sensors can also be integrally incorporated into the structure of the plastic container 10, or even included integrally as part of various means for sealing the plastic container 10. For example, such sensors can be incorporated in transparent windows or within a test probe funnel 182b, a test probe 182C, a funnel and tube 182f, or other test strip holders shown in FIG. 7. The illustrated test probes 182 can be attached to the containers 10, such as to access ports 180. The test probes 182 can be readily detached from the container 10 to complete testing elsewhere. The test probes 182 can also be used as separate testing devices when the probes 182 contain a test means, such as is shown for the test probes 182c and 182d. Various conventional test strips are illustrated in the test probes 182, such as pH strips and other general conventional chemical analysis strips.

More complicated tests can involve the release of one or more analytical reagents in the upper container section 16 or the subcompartments 24, such as, by opening or breaking a capsule 52 containing an analytical agent (see FIG. 2). This analytical reagent reacts with the specimen and analytical equipment, such as shown in FIG. 5, can then be used to carry out the tests. Various chemical reaction can be initiated with test chemicals and optical analysis equipment, such as the Color Eye 3000 (described before). Even the naked eye can be used in some cases to detect color changes through the optically transparent or translucent container 10 or the test probe 182.

In another form of the invention, the plastic container 10 further includes a substantially rigid element which can be disposed in at least one particular portion of the flexible container. For example, the rigid element can be a piece of cylindrical tubing 54, a sample cup 65, or a conical pipette 66, as shown in FIG. 1. One can also choose to have a snug fit for the lower portion of the cylindrical tubing 54, the sample cup 65, or the conical pipette 66 in order to establish a seal to the flexible container 10. This seal surface will allow specimen handling such that no leakage of the undesired specimen occurs other than by a path through the tubing 54, the sample cup 65 or the pipette 66.

Such a rigid or semi-rigid element structure advantageously also provides a predetermined shape for allowing shape sensitive mechanical handling of the specimen. By establishing this predetermined shape, the specimen can be handled by analytical processes which require fitting the container portion which holds the specimen into a mating receptacle of an analytical apparatus. For example, in the case of the rigid or semi-rigid element being the cylindrical tubing 64 (see FIG. 2), the specimen is collected in the right most container subcompartment 24 which is separated from the plastic container 10 by cutting along seal lines 60 and 62. A resulting separated container subcompartment 58 containing the specimen and the cylindrical tubing 64 can then be directly inserted into test tube receptacles of a specimen processing apparatus (see FIGS. 6 and 9). Using such an analytical processing station, an automated specimen sampling probe described hereinbefore can be used to retrieve a sample of the specimen for chemical analysis. Therefore, the substantially rigid cylindrical tubing 64 shown in FIG. 2 can even allow the unmodified use of specimen processing equipment for analysis of the specimen collected in the plastic container 10 of the invention. The size and shape of the rigid element can be adjusted for the amount of fluid or specimen collected.

Figure 9:
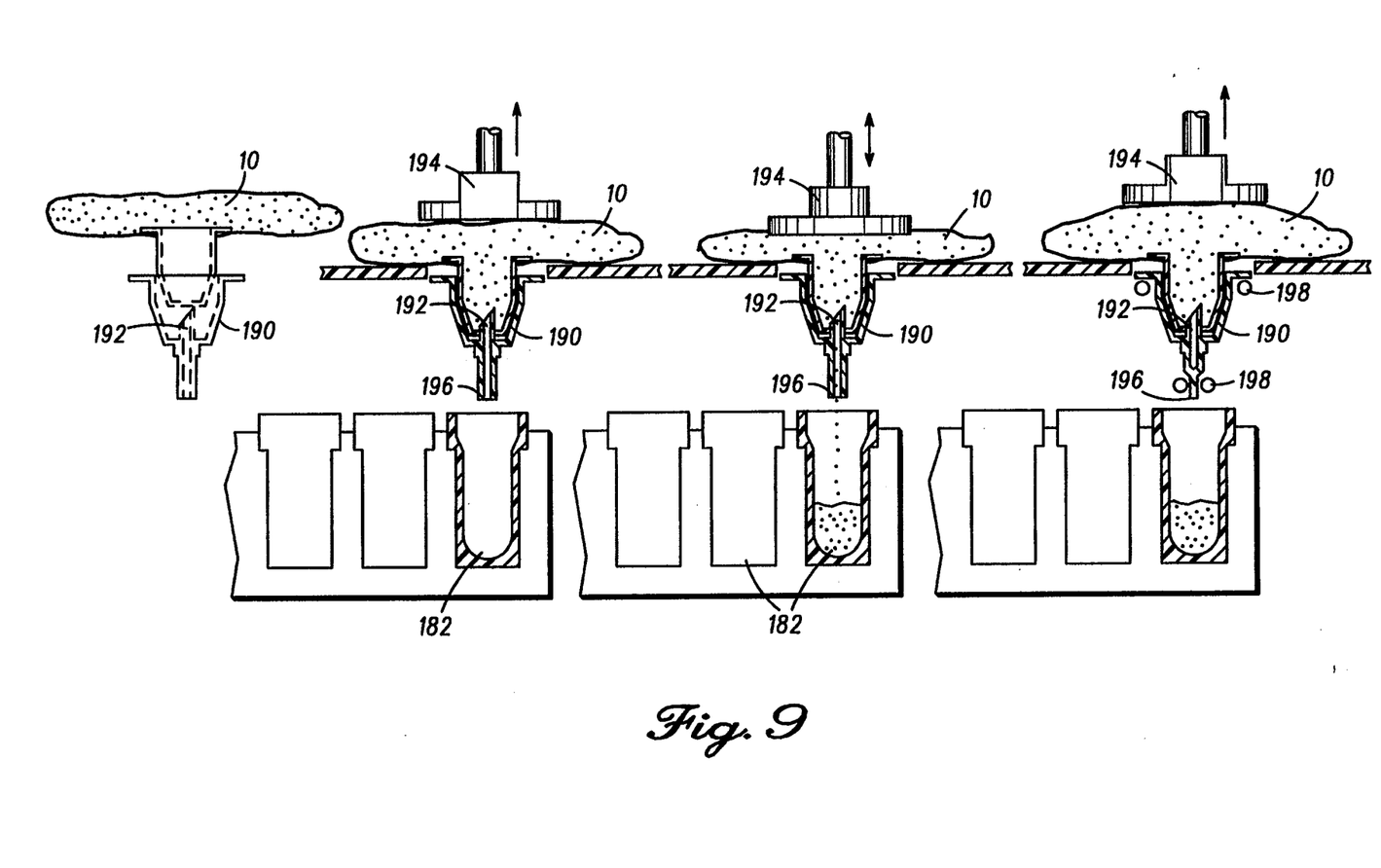
FIG. 9 illustrates various stages of operation of another form of puncture and draining feature of an automated fluid analysis system.

As mentioned hereinbefore, in the embodiments of FIG. 7 the specimen can be collected in the probe containers 182, which can then be sealed to enclose the specimen. This specimen can later be analyzed by a technician or processed by an automated analysis apparatus, such as is shown in FIGS. 6 and 9. The technician can also choose to dispense the specimen by squeezing displaceable container 182C causing controlled substance removal for analysis. Alternatively, the container 182C can be used to collect the fluid specimen by its vacuum action, with a test strip allowing analysis of the specimen.

In another variation of this embodiment as shown in FIGS. 6 and 9, the fluid specimen in the plastic container 10 can be analyzed by an automated system wherein the specimen is accessed through a port 154 sealingly coupled to the plastic container 10. The plastic container 10 is being transported along conveyor 156 having openings 158 which accept the ports 154. At selected locations along the conveyor 156, a sampling station 159 accesses the fluid specimen in the plastic container 10 by engaging a piercing element 160 to the port 154 shown in detail in FIG. 6B. As shown in FIG. 6A, the piercing element 160 includes a sharp protrusion 162, and the piercing element 160 is moved by engagement device 163 causing the protrusion 162 to pass through the top seal of the port 154. Penetration of the port 154 causes the fluid specimen to pass through orifices 164 into test receptacle 166 (such as a test tube, or any one of the probe or test containers 182 shown in FIG. 7) disposed in an analyzer housing 168. The transfer of a fluid specimen from the plastic container 10 can also be assisted by a mechanical press 170 which applies pressure to force the fluid specimen into the test receptacle 166. Once sufficient fluid specimen has been accumulated in the test receptacle 166, the engagement device 163 sealingly reengages the piercing element 160 to the port 154. The engagement device 170 is then retracted leaving piercing element 160 sealingly engaged with the port 154. The fluid specimen in the test receptacle 166 is subsequently transported into an analyzer (not shown) for performing appropriate tests. The sampled and resealed plastic container 10 is transported by the conveyor 156 to a next selected location, such as a storage area or to another test station where a different test can be performed on the already accessed specimen or another one of the redundant fluid specimens in another subcompartment of the plastic container 10.

Another form of the automated analysis system is shown in FIG. 9 wherein a penetrating-sealing pipette 190 is shown. The pipette 190 includes a penetration element 192 for penetrating the plastic container 10, A means for applying pressure or applying a suction force, such as contact member 194, enables application of pressure or vacuum force to the plastic container 10 having a liquid specimen therein. The pipette 190 can be positioned below the specimen containing plastic container 10; the pipette penetration element 192 is brought into contact with the container 10 to pierce the flexible wall causing the fluid specimen to pass into one of the probe containers 182. After dispensing the liquid specimen the pipette 190 is sealed at bottom tip 196 by a sealing means, such as a thermal sealing element 198. By operation in this manner the liquid specimen does not come into contact with the technician and does not escape into the environment.

Figures 3A, 3B, 3C, 3D, 3E:
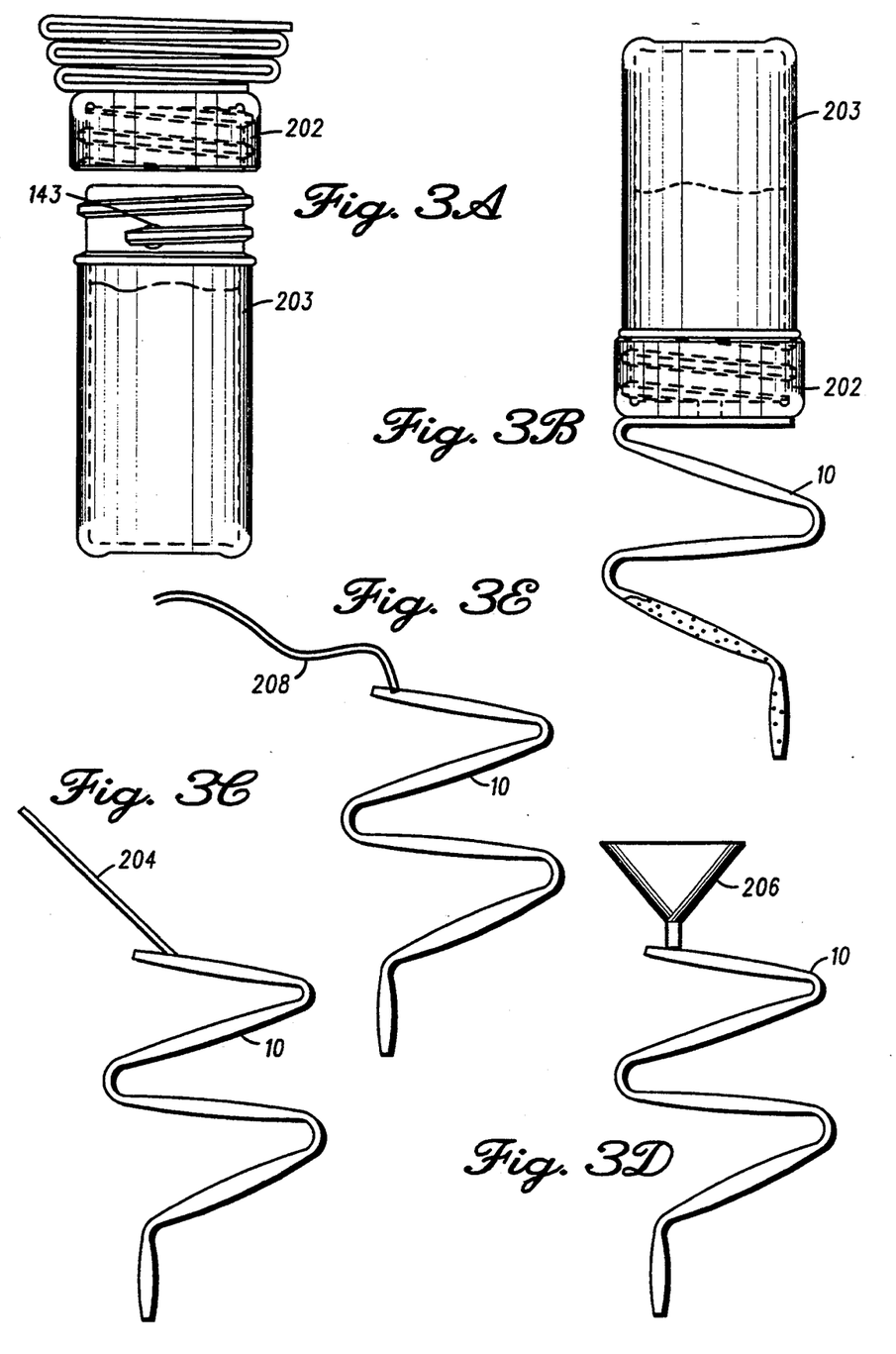
FIG. 3A illustrates a folded plastic bag coupled to a bottle cap disposed above a bottle containing a fluid specimen.
FIG. 3B shows the transfer of the fluid specimen from the bottle to the plastic container or vice versa.
FIG. 3C shows a catheter coupled into a plastic container.
FIG. 3D illustrates a funnel coupled into a plastic container and FIG. 3E shows a piece of tubing coupled into a plastic container.
Figure 4A:
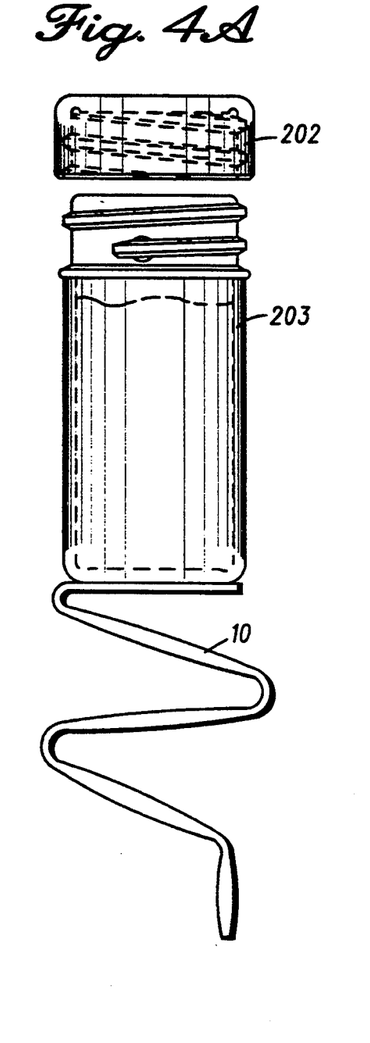
FIG. 4A illustrates a plastic container coupled to the bottom of a bottle having a hole allowing the fluid specimen to be transferred to the plastic container and FIG. 4B shows a plastic container coupled to the side of a bottle having a hole allowing the fluid specimen to be transferred to and from the plastic container.
Figure 4B:
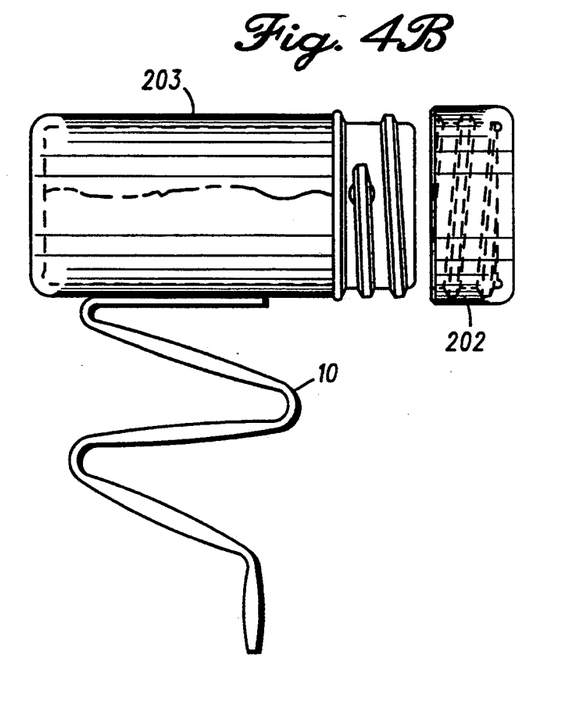

In another form of the invention, the multicompartment plastic container 10 can be coupled to general means for transferring the specimen to the container 10. The transfer means can, for example, include a bottle cap 202 (FIG. 3b) a catheter 204, (FIG. 3c), a funnel 206 (FIG. 3d) or tubing 208 (FIG. 3e). These various transfer means can be connected at any desired location on the plastic container 10, such as the top, bottom or side of the plastic container 10. These transfer means allow the convenient transfer of the specimen from the source (e.g., a remote or local container or transfer lines) to the plastic container 10. The transfer means can also be used to couple directly into the source for a less conventional, but sometimes necessary, collection of the specimen.

Some of these transfer features allow the collection of the specimen independent of the subject and even processing of the specimen before transfer into the container 10. For example, (a) the bottle cap 202 and attached plastic container 10 can be joined to a bottle 203 which contains the specimen to be transferred, (b) the funnel easily allows pouring the specimen into the plastic container 10, (c) the catheter 204 enables the transfer of the specimen directly and (d) the tubing allows the general transfer of the specimen from any source, such as a reservoir (not shown). These transfers therefore allow the hybrid use of the multicompartment plastic container 10 with more conventional devices (e.g., bottles) for accumulation of specimens.

While preferred embodiments of the invention have been shown and described, it will be clear to those skilled in the art that various changes and modifications can be made without departing from the invention in its broader aspects as set forth in the claims provided hereinafter.

What is claimed is:

1. A system for sampling a fluid specimen for testing in an analysis station, comprising:
    a container for holding said specimen, said container having an access port sealingly coupled to said container;
    means for accessing said access port for allowing said fluid specimen to be removed from said container, said means for accessing and said container being positioned one relative to the other;
    means for engaging said accessing means to said access port with said accessing means having a single accessing element both for removably engaging said access port to open said access port and for allowing removal of said fluid specimen;
    sealing means for reseating said container after accessing said fluid specimen and remaining with said access port after removal of said fluid specimen, said sealing means being an integral part of said means for accessing; and
    means for collecting said fluid specimen transferred through said access port for subsequent analysis, said means for collecting including a specimen test receptacle.

2. A system for sampling a fluid specimen for testing in an analysis station, said system comprising:
    a plastic container for holding said fluid specimen, said plastic container having an access port sealingly coupled to said plastic container;
    means for accessing said access port for allowing said fluid specimen to be removed from said container and said container being positioned relative to said accessing means;
    means for engaging said accessing means to said access port of said container to allow opening of said access port, thereby allowing said fluid specimen to be transferred from said container;
    means for applying an external positive pressure to said container to assist in the transfer of said specimen from said container;
    plastic sealing means for resealing said accessing means after accessing said fluid specimen and said accessing means remaining with said access port after removal of said fluid specimen, said sealing means further including means for heating said accessing means to perform the resealing operation; and
    means for collecting said fluid specimen transferred through said access port for subsequent analysis, said collecting means including a specimen test receptacle.

3. A system for sampling a fluid specimen for testing in an analysis station, said system comprising:
    a plastic container for holding said specimen, said container having an access port sealingly coupled to said container;
    means for accessing said access port for allowing said fluid specimen to be removed from said container, said means for accessing and said container being positioned one relative to the other;
    means for engaging said accessing means to said access port with said accessing means having a single accessing element both for removably engaging said access port to open said access port and for allowing removal of said fluid specimen;
    means for applying an external positive pressure to said plastic container to assist in a transfer of said specimen from said container;
    sealing means for resealing said container after accessing said fluid specimen and remaining with said access port after removal of said fluid specimen, said sealing means being an integral part of said means for accessing; and
    means for collecting said fluid specimen transferred through said access port for subsequent analysis, said means for collecting including a specimen test receptacle.

4. A system for sampling a fluid specimen for testing in an analysis station, said system comprising:
    a plastic container for holding said fluid specimen, said plastic container having an access port sealingly coupled to said plastic container;
    means for accessing said port for allowing said fluid specimen to be removed from said container and said container being positioned relative to said accessing means;
    means for engaging said accessing means to said access port of said container to allow opening of said access port, thereby allowing said fluid specimen to be transferred from said container;
    plastic sealing means for resealing said accessing means after accessing said fluid specimen and said accessing means remaining with said access port after removal of said fluid specimen, said sealing means further including means for heating said accessing means to perform the resealing operation; and
    means for collecting said fluid specimen transferred through said access port for subsequent analysis, said collecting means including a specimen test receptacle.

5. The system as defined in claim 4 wherein said accessing means comprises a piercing element transferably coupled to said means for engaging.

6. The system as defined in claim 3 wherein said accessing means comprises a piercing element transferably coupled to said means for engaging.

7. The system as defined in claim 1 wherein said accessing means comprises a piercing element transferably couple to said means for engaging.

* * * * *